United States Patent
Degn et al.

(10) Patent No.: US 6,558,630 B1
(45) Date of Patent: May 6, 2003

(54) DOSING UNIT AND A METHOD OF CONTINUOUS INTRODUCTION OF LIQUID SOLUTION SAMPLES INTO A SYSTEM

(76) Inventors: Hans Degn, Østbirkvej 19, DK-5240 Odense NØ (DK); Henrik Ørsnes, Sdr. Boulevard 222, 2. sal, DK-5000 Odense C (DK); Thomas Graf, Svenstrupvej 24A, DK-5260 Odense S (DK)

( * ) Notice: Subject to any disclaimer, the term of this patent is extended or adjusted under 35 U.S.C. 154(b) by 0 days.

(21) Appl. No.: 09/529,714

(22) PCT Filed: Oct. 20, 1998

(86) PCT No.: PCT/DK98/00453
§ 371 (c)(1),
(2), (4) Date: Jun. 14, 2000

(87) PCT Pub. No.: WO99/20329
PCT Pub. Date: Apr. 29, 1999

(30) Foreign Application Priority Data

Oct. 20, 1997 (DK) .......................... 1997 01195

(51) Int. Cl.[7] .............................. B01L 3/02; B01L 3/00; G01N 1/10; G01N 1/00; C12M 1/34; C12M 3/00; F16C 33/74; B05C 1/06; B05C 1/08

(52) U.S. Cl. .................. 422/100; 422/99; 436/180; 436/174; 435/287.3; 384/152; 384/156; 118/261

(58) Field of Search .................... 422/100, 99, 68.1; 435/287.3, 309.1; 250/288; 436/180, 178, 174; 118/261; 384/152, 153

(56) References Cited

U.S. PATENT DOCUMENTS 3,745,972 A * 7/1973 Thettu .................. 118/261
3,989,005 A * 11/1976 Bowler et al. ............... 118/261
4,048,919 A * 9/1977 Woods ........................ 101/148
4,076,982 A    2/1978 Ritter
4,091,765 A * 5/1978 Lowthorp et al. ........... 118/261
4,588,470 A * 5/1986 Abegglen .................... 118/259
4,705,616 A   11/1987 Andresen
4,789,639 A * 12/1988 Fleming ..................... 206/361
4,879,458 A   11/1989 Brunfeldt
5,080,013 A *  1/1992 John ........................... 101/169
5,194,226 A *  3/1993 Tomoff et al. .............. 422/100
5,525,302 A *  6/1996 Astle ........................... 422/100
5,580,434 A   12/1996 Robotti
5,608,217 A    3/1997 Frazen
5,736,105 A *  4/1998 Astle ........................... 422/100
5,770,160 A *  6/1998 Smith et al. ................. 422/100
5,814,277 A *  9/1998 Bell et al. ...................... 422/67
6,123,418 A *  9/2000 Wakahara et al. ............. 347/55
6,126,275 A * 10/2000 Kagayama ..................... 347/55
6,151,047 A * 11/2000 Desie et al. ................... 347/55
6,196,666 B1 *  3/2001 Kitamura ....................... 347/55
6,264,308 B1 *  7/2001 Shimada ....................... 347/55

FOREIGN PATENT DOCUMENTS

| EP | 0433936 | 6/1991 |
|----|---------|--------|
| GB | 2213586 | 8/1989 |
| WO | 8502490 | 6/1985 |
| WO | 9111014 | 7/1991 |
| WO | 0635710 | 1/1995 |
| WO | 9527212 | 10/1995 |

* cited by examiner

*Primary Examiner*—Jill Warden
*Assistant Examiner*—Brian R Gordon
(74) *Attorney, Agent, or Firm*—Ladas & Parry

(57) ABSTRACT

A device and method of continuous introduction of liquid solution samples into a system from a chamber containing the solution.

10 Claims, 5 Drawing Sheets

DOSING UNIT AND A METHOD OF CONTINUOUS INTRODUCTION OF LIQUID SOLUTION SAMPLES INTO A SYSTEM

FIELD OF THE INVENTION

The present invention relates to a dosing unit for continuous introduction of liquid solution samples into a system. Moreover it relates to a method of continuous introduction of liquid solution samples into a system from a chamber containing the solution.

BACKGROUND OF THE INVENTION

A number of arrangements are known for dosing small samples of liquid into a system in the form of a treatment apparatus. These will be explained later. First an explanation of the prior art arrangements in association with mass spectrometry will be given.

U.S. Pat. No. 4,705,616 describes a process and an interface probe for discharging chemicals from one end of a capillary tube into a mass spectrometer. Chemicals are fed into the other end of the capillary tube by a valve comprising a housing and a rotable member inside the housing. The rotable member, which is rotable between two positions, is constructed with a transversal fluid passage by which chemicals can be transported from a reservoir into the capillary tube. In one of the two positions, where the fluid passage is parallel to the capillary tube, the fluid passage allows a continuous flow of chemical from a reservoir into the capillary. In the other position, where the passage fluid is perpendicular to the capillary, chemicals from a second reservoir are fed into the passage, but these chemicals are only released when the rotable member is back in the first position. Thereby, an intermittent operation is obtained.

Continuous mass spectrometric monitoring of a reaction mixture or the effluent from a separation device requires continuous introduction of a minute. stream of sample into the vacuum of the mass spectrometer. Established techniques use either pervaporation through a solid polymer membrane or mass flow through a capillary or porous membrane for this purpose. In addition a mechanical device, the moving belt, has been designed to introduce continuously the remnant of evaporated sample. Each technique has its own advantages and disadvantages and no single technique has universal applicability.

In the pervaporation technique, membrane inlet mass spectrometry, the sample is separated from the vacuum of the mass spectrometer by a thin, solid polymer membrane. Compounds such as gases and organic volatiles diffuse through the membrane into the mass spectrometer where they are ionized and give rise to mass spectrometric signals, which are proportional to the activities of the compounds in the liquid or gaseous sample. Ionisation usually takes place by collision with electrons emitted from a hot filament. Electron impact ionisation (EI) causes extensive disintegration of analyte molecules to form fragment ions which can be used to identify the analyte. Chemical ionisation, where analyte molecules are ionized by capturing charges from The path through which analyte travels from the sample to the vacuum has three stages, namely the unstirred layer (Nernst layer) of liquid sample adjacent to the membrane, the membrane itself and the space in vacuum from the inside of the membrane to the ion source. The detection limit of the measurement is mainly determined by the stage that has the highest resistance to the transport process and the response time is mainly determined by the stage where the transport process has the longest relaxation time. Both limitations are often located in the membrane stage. The permeability of a polymer membrane is a product of the solubility of the compound in the membrane material and the mobility of the dissolved compound. Whereas high solubility in the membrane material is favorable for the sensitivity of the measurement, it is unfavorable for the response time because an increased accumulation of analyte in the membrane leads to an increased relaxation time of the transport process. Thus FAX high sensitivity and rapid response are mutually exclusive as far as these properties are determined by the membrane. The transport of analyte from the inside of the membrane to the ion source takes place by molecular flow. Molecules that collide with the walls surrounding the flow path may be absorbed to the walls and later desorbed. This gives a contribution to the response time which depends strongly on the volatility of the analyte.

Since only small amounts of gases and volatiles enter the mass spectrometer, the pervaporation technique is very clean and can be carried on for long periods of time without the need for internal cleaning of the mass spectrometer. Another advantage is that measurements with the pervaporation technique of favoured compounds, i.e. compounds that partition in favour of the membrane material, do not require any pretreatment of the sample. Measurements can be done in cell suspensions and in strongly acidic or alkaline solutions. The sensitivity of the pervaporation technique for a compound which partitions strongly in favour of the membrane may be very high. However, the response time may be too long for practical use in monitoring of reaction systems. In addition the accumulation of analyte in the membrane may change the properties of the membrane material leading to a non-linear response.

Whereas the solid membrane excludes a large class of compounds which do not readily pervaporate through the membrane material, a mass flow technique utilizing a porous membrane allows sample to enter the mass spectrometer with little change in composition. The flow through a porous membrane is a combination of laminar and turbulent flow depending on the pore size of the membrane material. This type of flow is much faster than diffusion through a solid membrane and, consequently, the response time may be much shorter with a porous membrane than with a solid membrane. Another difference is that because the flow through the porous membrane is not selective, no depletion of solute takes place in the sample adjacent to the surface of a porous membrane as it occurs at a solid membrane. A major drawback of mass flow techniques in general is that comparatively large amounts of material including salts and other non-volatiles enter and accumulate in the mass spectrometer making frequent cleaning necessary. In addition filtration of the sample is often necessary since clogging may otherwise occur. The most common use of porous membrane inlets is in the field of electrochemistry. Electron impact as well as chemical ionisation is used.

Continuous fluid introduction through a capillary includes thermospray, electrospray, particle beam and continuous-flow fast atom bombardment (CF-FAB). Thermospray operates by the generation of a fine mist of droplets from the sample solution and the evaporation of the solvent from the droplets to yield ions of the analyte. Enrichment is achieved because much of the solvent is evaporated and pumped away, whereas the analyte molecules, being charged, can be electrically focused to enter the analyzer. In the particle beam technique the remnant after vaporization of the droplets forms particles which are guided into the analyzer by translational momentum. In CF-FAB the sample liquid is not nebulized but mixed with glycerol and made to flow onto the target area of a xenon atom source in the mass spectrometer.

The moving belt technique for continuous sample introduction is neither a pervaporation technique nor a mass flow technique. It belongs to a third category where sample is brought into the mass spectrometer by mechanical transport. Sample is applied to a moving belt from where the solvent evaporates and the remnant, sticking to the surface of the belt, is dragged into the mass spectrometer through a vacuum lock.

As it occurs from the above a number of drawbacks are associated with the prior art systems.

It is the purpose of the present invention to provide a unit and a method in which these drawbacks are obviated and which provides for a new and simple arrangement for continuous sample introduction in which it is possible in a simple and reliable manner to adjust the rate of the sampling of different types of solution.

According to the present invention this is obtained with a unit mentioned above wherein a moving member is provided in a chamber containing said solution, said member is pressed against a gasket surrounding the inlet opening of the system, the member is connected with drive means for moving it whereby a sample of the solution adhered to the surface is dragged past the gasket into the inlet.

SUMMARY OF THE INVENTION

The method according to the present invention for continuous introduction of liquid solution samples into a system from a chamber containing the solution wherein the liquid adhering to a surface of a moving member provided in said chamber is dragged past a gasket surrounding an inlet to the system by activating drive means connected with said member.

The unit is a simple mechanical means of transportation for the sample which is obtained on the surface as the member is submerged in the solution. Therefore, the member will drag small quantities of the solution past the gasket when activating the drive means. This activation can be a continuous or intermittent drive. The amount to be introduced in the apparatus is adjusted in simple manner by regulation of the movement rate of the member, the pressure exerted on the member and the size thereof. Moreover, it is easy to adapt the member to different types of solution by amending the surface properties and the force used to press the member against the gasket.

According to a preferred embodiment the system is a treatment apparatus in the form of an analysis apparatus where the inlet opens into an analysis chamber, and especially a mass spectrometer having a vacuum chamber wherein the analysis is effected. The unit may also be used in a system comprising a living organism, e.g. for dosing a medicine into the human body.

The moving member is preferably a rotation member in the form of a ball and the drive means is a motor having a shaft which is connected with the ball which co-operates with the gasket in form of a circular flange being easy to manufacture. Preferably the rotation member is made of steel having a polished surface having cavities of a mean depth of 0.5 micron and the gasket is a polymer gasket manufactured from Teflon containing graphite in an amount between 20 and 30%. Alternatively, the member is made of ceramic or crystalline materials, e.g. a ruby.

It is also possible that the moving member is a reciprocating member having a flat, curved or circular surface for contact with the gasket.

In order to obtain sample rates which are convenient for mass spectrometry of a variety of compounds in an aqueous solution it is preferred that the steel ball has a diameter of between 8 and 30 mm, preferably of between 10 and 20 mm and is rotated with a rotational rate of between 3 and 8 rpm, preferably of 5 rpm and that a pressure of between $5*10^{-5}$ and $5*10^{-7}$ mbar, preferably of $5*10^{-6}$ mbar is maintained during the sample analysis.

Because monitoring bioreactors is a particularly important field for continuous mass spectrometry the apparatus has been tested on a suspension of bakers yeast supplied with glucose. The production of ethanol could be recorded and the presence of cells did not disturb the measurement. The cavities in the surface of the ball seen with electron microscopy are too small to accommodate yeast cells. Measurements of dissolved compounds in suspensions of smaller cells such as bacteria may require a more finely polished ball.

The rotating ball inlet has the same field of applications as the other techniques for continuous sample introduction mentioned above. This is a wide and expanding field including the monitoring of industrial reactors and the environment. In certain hyphenated techniques such as liquid chromatography-mass spectrometry (LC-MS), where a conventional method for continuous sample introduction is utilized in connection with a separation techniques, the rotating ball inlet may possibly be used with advantage. The most important advantages of the rotating ball inlet compared to other devices for continuous sample introduction are simplicity and fast response.

Continuous mass spectrometric monitoring of solutes in water requires continuous introduction of a minute stream of sample into the vacuum of the mass spectrometer.

Different methods have been described above for continuous mass spectrometric monitoring of aqueous solutions. The above embodiments of the rotating ball unit have a sample cell which may be used for the determination of constant concentrations of solutes in aqueous samples or the monitoring of concentration transients in aqueous reaction mixtures. The chamber wherein the ball is situated may also be a reaction container, e.g. a fermenter, bioreactor or the like. Thus, it is possible to take out a sample directly from a container to the inlet of an analysis chamber or the like.

According to a further aspect of the invention a rotating ball unit is disclosed which is suited for continuous measurement on a sample stream. Apart from measurements on injected discrete samples this unit may be used for the monitoring of sample streams taken from reactors or effluents from liquid chromatographs and other separation apparatus. Because of the rapid response of rotating ball inlet mass spectrometry compared to membrane inlet mass spectrometry, the flow through cell proposed is better suited than a membrane inlet flow cell for the use in stopped flow mass spectrometry.

BRIEF DESCRIPTION OF THE DRAWING

The invention will now be explained in further detail with reference to the accompanying schematic drawing, in which

FIG. 1 illustrates a unit comprising a steel ball of 20 mm cross section 1 which is attached to a shaft 2 which is fixed to a gear motor 3 (Maxon Motor, Interelectric AG, Sachseln, Switzerland) through a flexible joint 4. The ball is pressed by the force of a spring 5 against a Teflon gasket 6 situated at the outer circumference of an inlet of 7 mm diameter in a 74 mm conflate flange 7. The inlet leads to the vacuum chamber of a system in the form of a mass spectrometer 15. The ball is situated inside a sample cell 8 which is filled with a solution to be analyzed. Thus, the ball is submerged in said solution.

FIG. 2 shows the results of measurements on solutions of ethanol in water. Each point represents the mass spectrometric signal (m/z 31) when it had stabilized after the change of sample. It is seen that the measurement of ethanol in water was linear over almost 3 decades. In comparison it has been reported that the measurement of ethanol in water with membrane inlet mass spectrometry was linear through less than one decade. The calibration curves for several other compounds were determined with the rotating ball inlet and they were all found to be linear throughout the range measured.

FIG. 3 shows the result of recording the signal of ethanol (m/z 31) during an experiment where the content of the sample cell was changed rapidly from pure water to a dilute solution of ethanol in water and vice versa. It is seen that the signal stabilized within a few seconds after each change of sample. Similar measurements in an expanded time scale on aqueous solutions of several other compounds all yielded response times of less than 5 sec.

Figure 4:
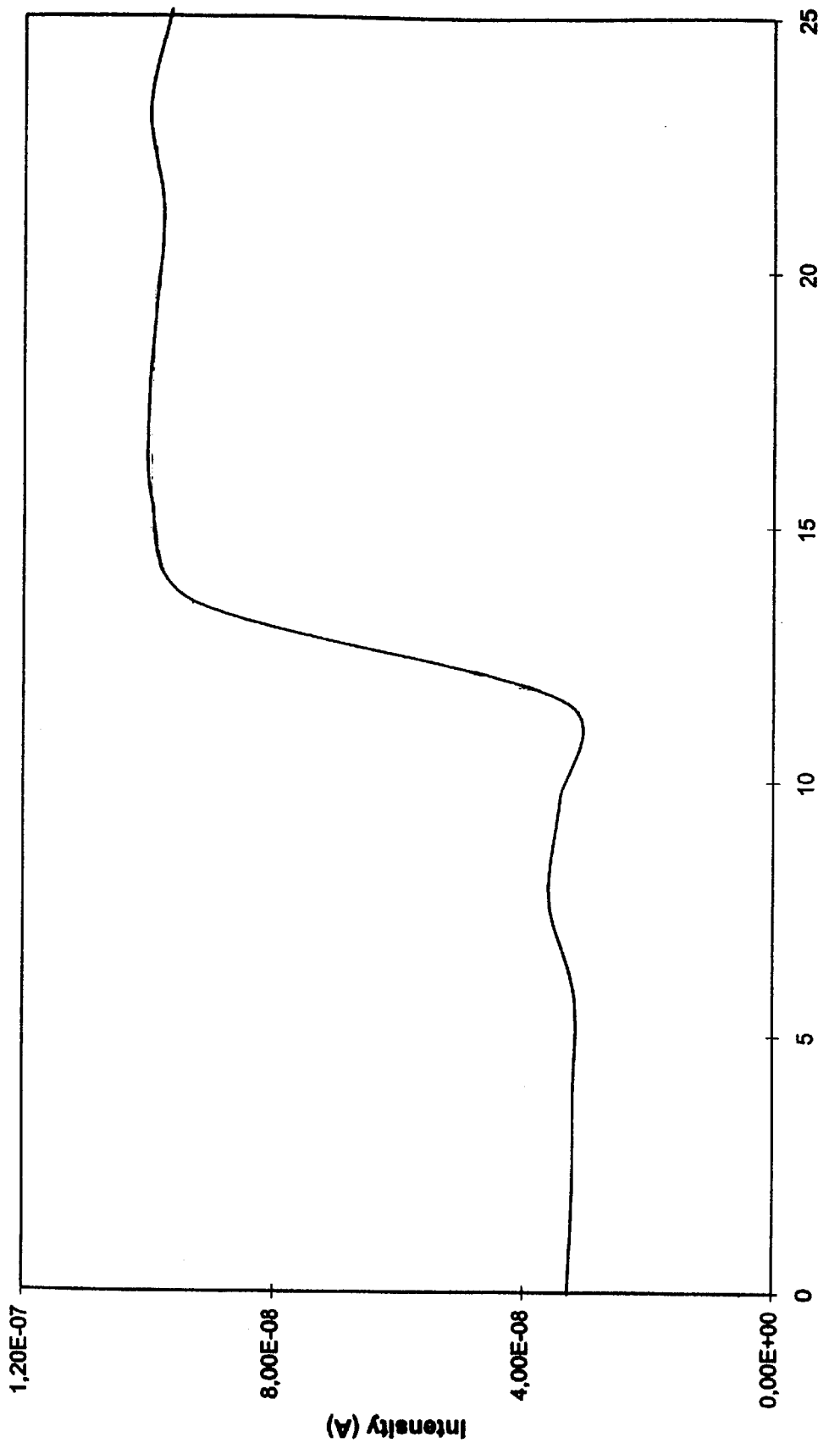
FIG. 4 illustrates a single ion monitoring of isopropyl alcohol at m/z 45, wherein the content of the sample cell was switched between pure water and a 13 mM solution of isopropyl alcohol in water.

An example where the sample was switched from pure water to a dilute solution of isopropyl alcohol (m/z 45) is shown in FIG. 4. The rise time was less than 2 sec. This is far better than what can be achieved with a pervaporation technique where the rise time of isopropyl alcohol would be in the order of minutes. The superior response time of the rotating ball inlet is due to the fact that there are no contributions to the response time from transport through an unstirred layer and a membrane.

The mechanical transport of sample from the outside to the inside of the vacuum chamber by the help of the rotating ball is much faster than diffusion through a membrane. The contribution to the response time due to adsorption and desorption at the surfaces during the transport inside the vacuum chamber is, however, not affected by the substitution of the membrane with a rotating ball.

Figure 6:
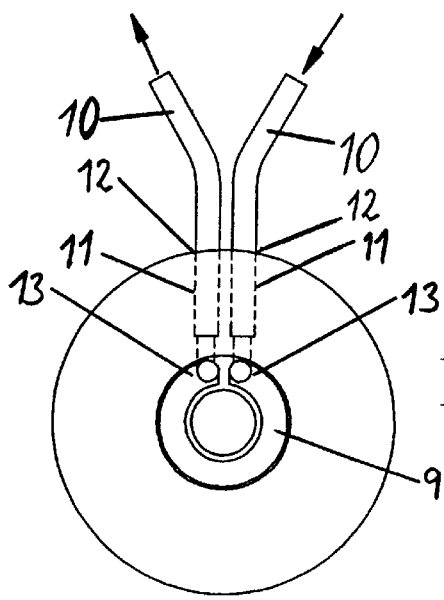
FIG. 6 is an enlarged view of the gasket.
Figure 7:
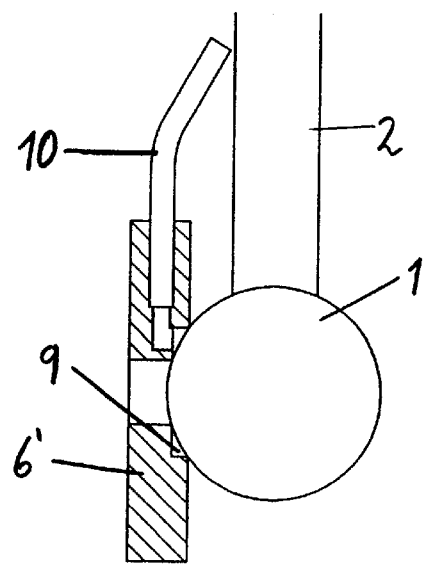
FIG. 7 is a side view of a part of the dosing unit illustrated in FIG. 5.
Figure 5:
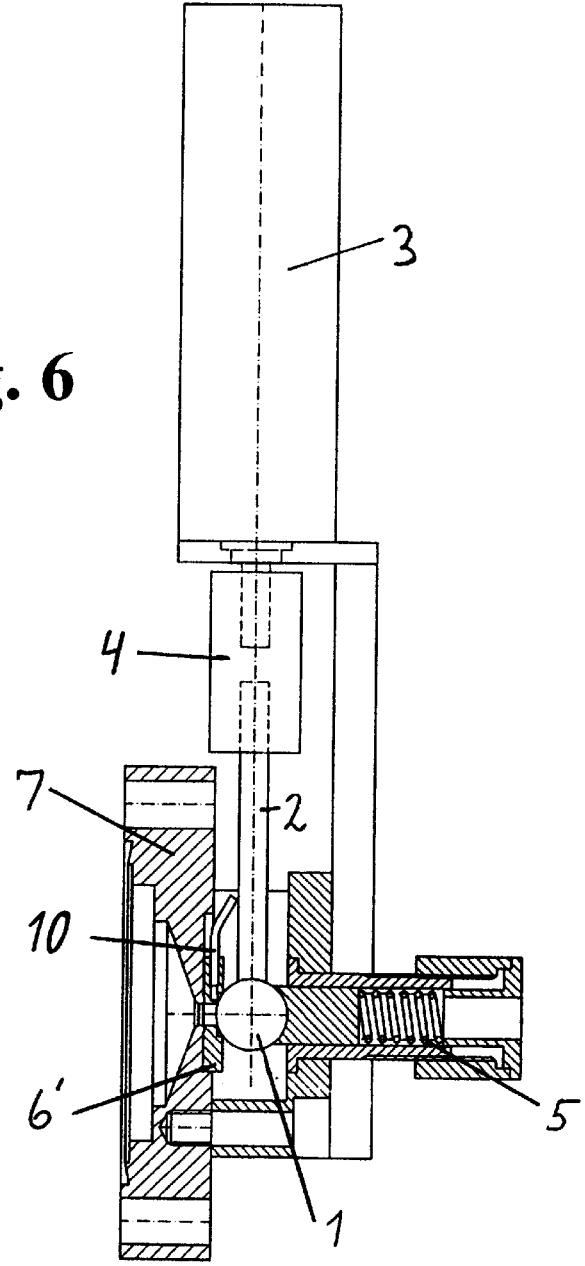
FIG. 5 is a view corresponding to FIG. 1 of a second embodiment for a dosing unit according to the present invention.

FIGS. 5, 6 and 7 show a second embodiment which may be said to be a flow through version of the rotating ball unit. The construction is very similar to the construction of the embodiment illustrated in FIG. 1. The ball 1 is a ruby ball of 10 mm cross section (Carl Zeiss, Oberkochen, Germany) which is fitted with a shaft 2 and attached to the gear motor 3 (Maxon Motor, Interelectric AG, Sachseln, Switzerland). The ball 1 is pressed by the force of the spring 5 against a Teflon gasket 6' situated at the outer circumference of a hole in a standard vacuum flange 7. However, it differs in that the gasket 6' (shown enlarged) has a horseshoe shaped groove 9 which, when covered by the ball 1, constitutes a channel for the sample stream. Steel capillaries 10 for inlet and outlet of the sample stream are inserted in holes leading from the periphery 12 of the gasket 6' to the two ends 13 of the groove 9. The gasket is made from Teflon containing 25% graphite.

Experiments

Figure 1:
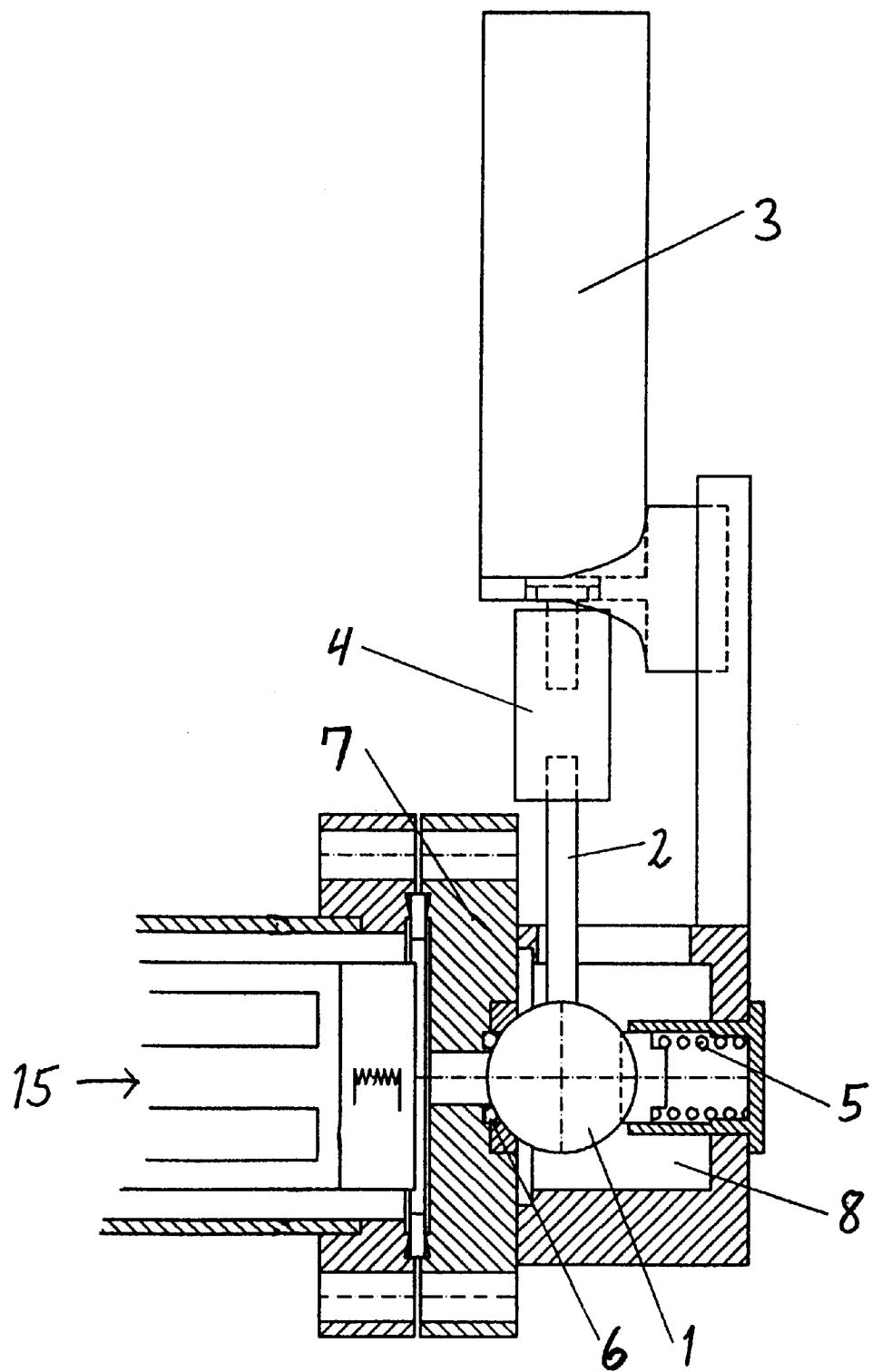
FIG. 1 is a view, partly in section, of an embodiment for a dosing unit according to the present invention and for use in association with a mass spectrometer.
Figure 2:
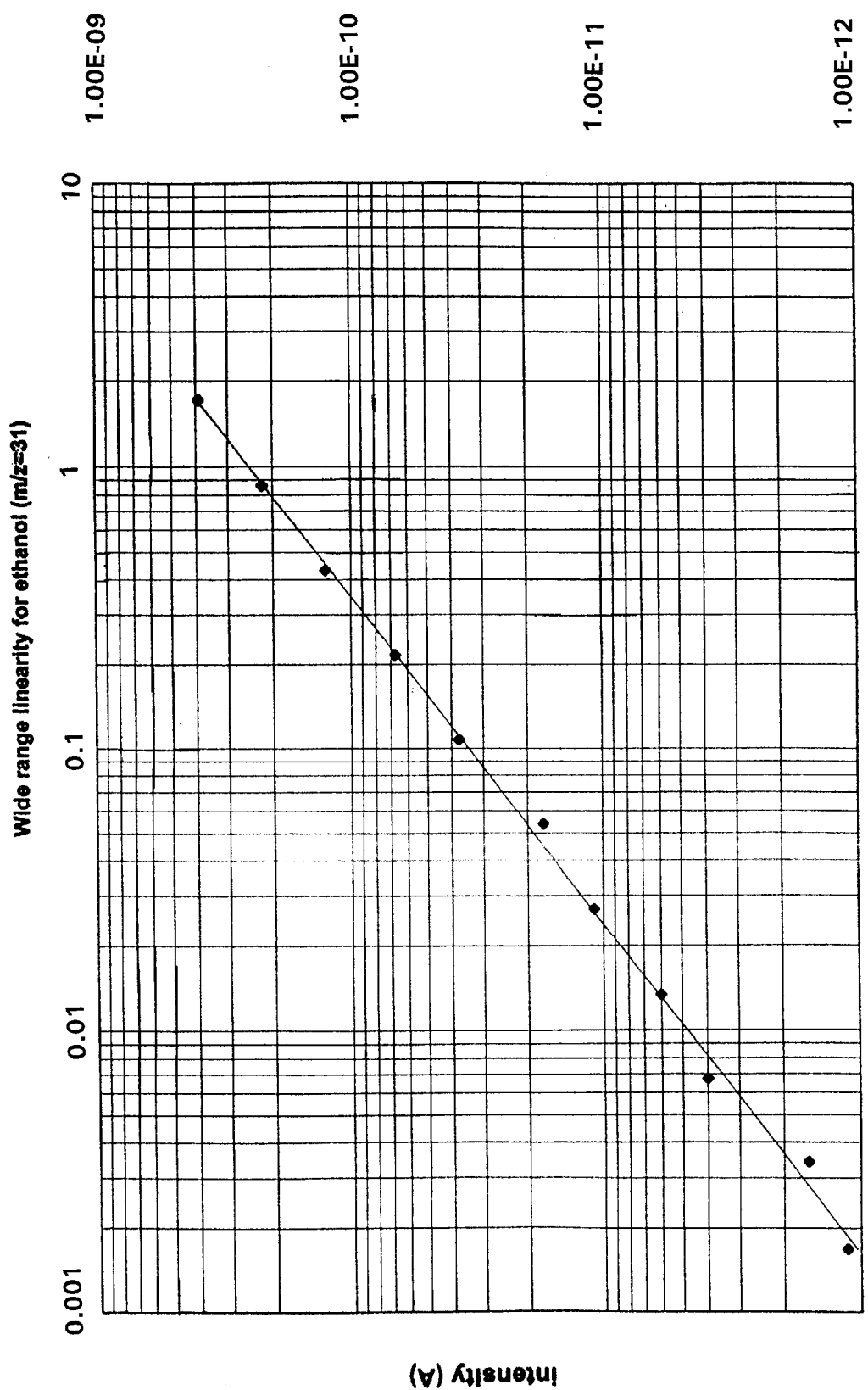
FIG. 2 is a logarithmic calibration curve for ethanol at m/z 31.
Figure 3:
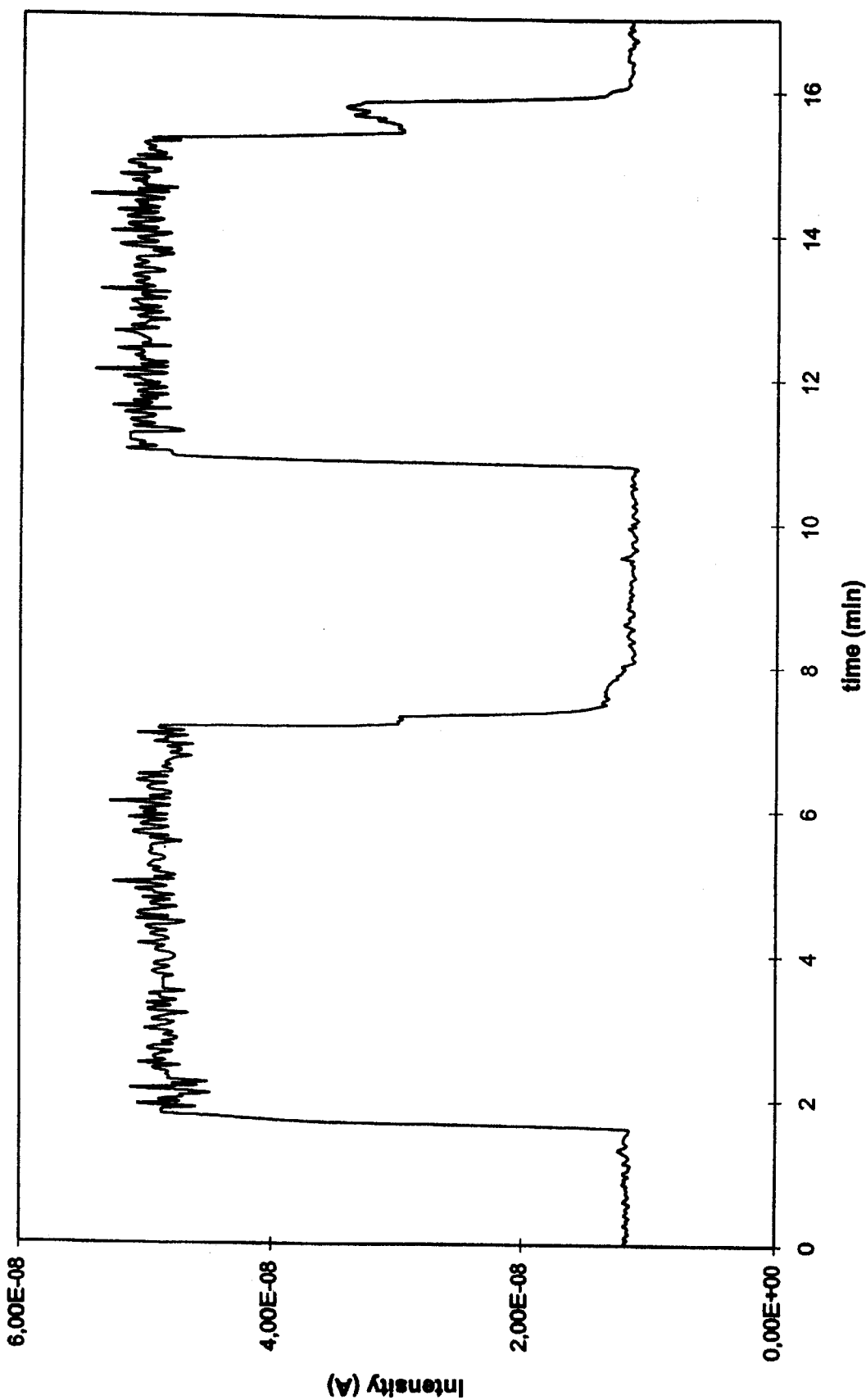
FIG. 3 illustrates a single ion monitoring of ethanol at m/z 31, wherein the content of the sample cell was switched between pure water and a 16.5 mM solution of ethanol in water.

The rotating ball inlet is shown in FIG. 1. A steel ball of ball bearing quality was fitted with a shaft and attached to a gear motor. The ball was pressed by the force of a spring against a Teflon gasket situated at the circumference of a hole in a vacuum flange. The flange was attached to a QGA-2 (ATOMKI, Debrecen, Hungary) quadrupole mass spectrometer with a mass range of 1–300 u. The ion source was an open EI source 30 cm remote from the inlet and ionisation was performed with 70-eV electrons. The ion current was detected with a Faraday cup. The quadrupole was orthogonally positioned relative to the inlet flange. The mass spectrometer was pumped with a diffusion pump. The apparatus was not thermostated.

Results and Discussion

When the vacuum pump was turned on and the ball was not rotating the pressure fell to about $2*10^{-7}$ mbar. When the sample cell was filled with water and the rotation of the ball was started the pressure increased to a level which depended on the rate of rotation. Periodic pressure spikes synchronous with the rotation of the ball were observed. These spikes were caused by scratches in the surface of the ball and were reduced to an insignificant level by ceramic polishing of the ball. After the ball had been polished, the pressure was stable at about $5*10^{-6}$ mbar for several hours at a rotation rate of 5 rpm. The subsequent mass spectrometric measurements were done in this pressure range. We have obtained electron microscopic pictures of the surface of the polished ball. The surface was seen to be covered with cavities of a mean depth of 0.5 $\mu$m. We assume that these cavities are responsible for the major part of the transport of sample into the mass spectrometer. We have no evidence pointing towards transport by selective adherence of sample molecules to the surface, but we do not exclude that this could be achieved by using a ball made from a different material.

Detection limits were determined for a variety of compounds in aqueous solution. Some results are shown in Table 1. It is seen that there is a significant correlation between the detection limit and the boiling point. In general the compounds which can be detected with our apparatus are those which are sufficiently volatile to leave the surface of the ball in significant quantity at room temperature. The lowest detection limit found was 0.1 mM. For the following reasons we believe this to be the lowest possible detection limit for any compound with the present version of the apparatus.

The rate of transport of analyte into the mass spectrometer with the rotating ball inlet is proportional to concentration rather than to activity. Therefore, the detection limits of all compounds which evaporate completely from the surface of the ball inside the vacuum chamber, are optimally ionized and enter the analyser and pass it with minimum loss should be identical and the lowest possible.

Judged from the data in Table I the lowest possible detection limit with the prototype apparatus used in this work is about 0.1 mM. It should be emphasized, however, that the detection limits were determined with a Faraday detector and up to a thousand fold improvement may possibly be achieved with the use of an electron multiplier. It also seems likely that the range of measurable compounds can be expanded with the use of one of the desorption techniques commonly employed in mass spectrometry.

TABLE 1

Detection limits for organic compounds in aqueous solution.

| Compound | Bp, °C. | Ion monitored, m/z | Detection limit, mmol/L |
|---|---|---|---|
| formaldehyde | −21 | 30 | 0.8 |
| methyl acetate | 57 | 43 | 1.3 |
| butyl amine | 77.8 | 30 | 0.1 |
| ethanol | 78.5 | 31 | 0.1 |
| isopropanol | 82.4 | 45 | 1 |
| acetic acid | 118 | 43 | 4.5 |
| glycerol | 290 | 61 | 10 |
| glucose | — | 72 | not detected |

What is claimed is:

1. A dosing unit in connection with a system for continuous introduction of liquid solution samples into said system, comprising a moving member in a chamber containing said solution, said member being pressed against a gasket surrounding an inlet opening of the system, the member being connected with drive means for continuously moving the member whereby a sample of the solution adhered to a surface of the member is dragged past the gasket into the inlet, wherein the system is an analysis apparatus.

2. The dosing unit in connection with a system according to claim 1, wherein the gasket is a polymer gasket.

3. The dosing unit in connection with a system according to claim 1, wherein the analysis apparatus comprises a mass spectrometer.

4. The dosing unit in connection with a system according to claim 1, wherein the moving member is a rotation member in the form of a ball and wherein the drive means is a motor having a shaft which is connected to the ball and wherein the gasket is annular.

5. The dosing unit in connection with a system according to claim 1, wherein the moving member is made of steel.

6. The dosing unit in connection with a system according to claim 1, wherein the moving member has a polished surface having cavities of a mean depth of 0.5 micron.

7. A method of continuous introduction of liquid solution samples into an analysis apparatus from a chamber containing the solution, where a moving member is provided in said chamber with drive means connected with said member and wherein said member is pressed against a gasket surrounding an inlet to the analysis apparatus, comprising the step of moving said moving member by said drive means in order to continuously drag said solution adhering to a surface of said moving member past said gasket into said analysis apparatus.

8. The method according to claim 7, wherein the analysis apparatus is a mass spectrometer and samples are introduced directly into a chamber held under vacuum thereby evaporating the samples.

9. The method according to claim 7, further comprising providing the liquid solution to said moving member in said chamber as a sample stream from at least one capillary.

10. The dosing unit in connection with a system according to claim 1, wherein the polymer gasket is made of polytetrafluoroethylene containing graphite in an amount between 20% and 30%.

* * * * *